United States Patent
Ruegenberg et al.

(10) Patent No.: US 9,624,923 B2
(45) Date of Patent: Apr. 18, 2017

(54) CONTROL ARRANGEMENT FOR CONTROLLING A PISTON PUMP UNIT FOR LIQUID CHROMATOGRAPHY

(71) Applicants: Gervin Ruegenberg, Munich (DE); Richard Schloderer, Krailling (DE); Werner Tuchan, Munich (DE)

(72) Inventors: Gervin Ruegenberg, Munich (DE); Richard Schloderer, Krailling (DE); Werner Tuchan, Munich (DE)

(73) Assignee: DIONEX SOFTRON GMBH, Germering (DE)

( * ) Notice: Subject to any disclaimer, the term of this patent is extended or adjusted under 35 U.S.C. 154(b) by 683 days.

(21) Appl. No.: 13/917,963

(22) Filed: Jun. 14, 2013

(65) Prior Publication Data
US 2013/0336803 A1 Dec. 19, 2013

(30) Foreign Application Priority Data
Jun. 19, 2012 (DE) .................. 10 2012 105 323

(51) Int. Cl.
*F04B 41/06* (2006.01)
*F04B 49/22* (2006.01)
(Continued)

(52) U.S. Cl.
CPC .............. *F04B 49/22* (2013.01); *F04B 23/06* (2013.01); *F04B 49/20* (2013.01); *G01N 30/22* (2013.01);
(Continued)

(58) Field of Classification Search
CPC .. F04B 1/02; F04B 23/06; F04B 49/20; F04B 49/065; F04B 49/08; F04B 2201/0201;
(Continued)

(56) References Cited

U.S. PATENT DOCUMENTS 4,137,011 A * 1/1979 Rock ................... F04B 11/0058
417/22
4,359,312 A * 11/1982 Funke ................. F04B 11/0058
417/18
(Continued)

FOREIGN PATENT DOCUMENTS

CN 101865109 A 10/2010
CN 102112741 A 6/2011
(Continued)

OTHER PUBLICATIONS

Office Action mailed Jul. 17, 2014 in corresponding JP application No. 2013-128658.
(Continued)

*Primary Examiner* — Charles Freay
(74) *Attorney, Agent, or Firm* — Timothy J. Ohara (57) ABSTRACT

A control arrangement for controlling a piston pump unit for liquid chromatography, in particular high-performance liquid chromatography, is described. The piston pump unit has at least two piston-cylinder units which operate cyclically in a phase-offset manner and generate, at an outlet port, a predetermined flow of a liquid medium to be delivered. A system pressure is established at the outlet port, irrespective of an associated fluid load resistance. The control arrangement is configured to record the pressure in the cylinder volume of at least a first of the at least two piston-cylinder units. During a measurement phase of the compression phase of the first piston-cylinder unit or during a measurement phase of the decompression phase of the first piston-cylinder unit, the control arrangement stops the drive device for the first piston-cylinder unit for a predetermined time period and in the process records measurement data which characterize the time profile of the pressure.

29 Claims, 5 Drawing Sheets

(51) Int. Cl.
  *F04B 49/20* (2006.01)
  *F04B 23/06* (2006.01)
  *G01N 30/32* (2006.01)
  *G01N 30/22* (2006.01)

(52) U.S. Cl.
  CPC ....... *G01N 30/32* (2013.01); *G01N 2030/326* (2013.01)

(58) Field of Classification Search
  CPC ......... F04B 2201/0202; F04B 2205/03; G01N 30/20; G01N 30/32; G01N 2030/326
  USPC .................. 417/2, 3, 426, 44.2, 22
  See application file for complete search history.

(56) References Cited

U.S. PATENT DOCUMENTS

| | | | |
|---|---|---|---|
| 4,492,524 A | | 1/1985 | Koch et al. |
| 4,681,513 A | | 7/1987 | Saito et al. |
| 4,752,385 A | | 6/1988 | Wilson |
| 4,753,581 A | | 6/1988 | Hiscock |
| 4,797,834 A | | 1/1989 | Honganen et al. |
| 4,980,059 A | * | 12/1990 | Barlow .................. G01N 30/36 210/101 |
| 5,108,264 A | * | 4/1992 | Abdel-Rahman ... F04B 11/0075 417/20 |
| 5,114,314 A | | 5/1992 | Fujimoto |
| 5,393,420 A | | 2/1995 | Hutchins et al. |
| 5,637,208 A | * | 6/1997 | Dourdeville .......... F04B 7/0007 137/565.13 |
| 5,897,781 A | * | 4/1999 | Dourdeville ............ F04B 13/00 210/101 |
| 8,182,680 B2 | * | 5/2012 | Herzog ............... F04B 11/0058 210/101 |
| 8,535,016 B2 | * | 9/2013 | Corral ................. F04B 11/0058 417/293 |
| 2008/0206067 A1 | | 8/2008 | De Corral et al. |
| 2010/0040483 A1 | | 2/2010 | Berger et al. |
| 2010/0275678 A1 | | 11/2010 | Herzog et al. |
| 2010/0299079 A1 | | 11/2010 | Berndt et al. |
| 2011/0132463 A1 | | 6/2011 | Witt et al. |
| 2011/0259451 A1 | | 10/2011 | Weissgerber |
| 2013/0104631 A1 | | 5/2013 | Tokuo et al. |

FOREIGN PATENT DOCUMENTS

| | | |
|---|---|---|
| DE | 3035770 C2 | 8/1984 |
| DE | 112005001673 | 10/2007 |
| EP | 0334994 B1 | 9/1992 |
| GB | 2433792 | 7/2007 |
| GB | 2446321 | 8/2008 |
| GB | 2446321 B | 8/2008 |
| GB | 2469899 | 5/2011 |
| JP | 07072130 | 3/1995 |
| JP | 2007113432 | 5/2007 |
| JP | 2012032187 | 2/2012 |
| WO | 2006017121 A2 | 2/2006 |
| WO | 2006103133 A1 | 10/2006 |
| WO | 2010124741 A1 | 11/2010 |
| WO | WO 2013/026446 * | 2/2013 |

OTHER PUBLICATIONS

Search Report mailed Aug. 11, 2014 in corresponding CN application No. 201310336415.1.

Foley et al., "Unavoidable Flow-Rate Errors in High-performance Liquid Chromatography," J. of Chromatography, 478, 287-309, 1989.

* cited by examiner

Fig. 1

Prior Art

Fig. 2

Prior Art

CONTROL ARRANGEMENT FOR CONTROLLING A PISTON PUMP UNIT FOR LIQUID CHROMATOGRAPHY

FIELD OF THE INVENTION

The invention relates to a control arrangement for controlling a piston pump unit for liquid chromatography, in particular high-performance liquid chromatography.

BACKGROUND

High-performance liquid chromatography (HPLC) is used to separate liquid samples into their constituent parts by means of a chromatography column (known as a column in the following text). In this case, the separation performance of the column depends inter alia on the length thereof and on the particle size of the packing material. For separation which is as good as possible, columns having a sufficient length and a small particle size are required. Such columns have high flow resistance and therefore require considerably higher pressures than conventional columns for operation.

Furthermore, sufficiently rapid separation is desired in order to allow a high sample throughput. This requires a high flowing speed in the column, with the result that the counter-pressure of the column likewise increases.

For these reasons, modern, efficient HPLC installations operate with increasingly high pressures. While pressures under 100 bar were usual in the early stages of HPLC, current HPLC pumps can sometimes deliver pressures above 1000 bar. This trend is continuing and is causing a requirement for HPLC pumps which can deliver pressures considerably higher than 1000 bar.

A basic requirement of pumps for HPLC is that the flow rate, called flow in the following text, has to be delivered as far as possible without pulsing and in a reproducible manner. In the case of gradient pumps, which are capable of mixing two or more different liquid media (also known as solvents in the following text) in a ratio which is settable in a defined manner, the mixing ratio also has to be maintained in a precisely defined manner and may not have any undesired fluctuations.

SUMMARY

In a first embodiment, the invention is based on the finding that, by briefly stopping the piston during the compression phase and recording the time profile of the pressure during this measurement phase, it is possible to obtain information which can be used to determine a correction dependence $s_{corr}$ for controlling the piston or pistons in the delivery phase following the compression phase or in the compensation phase (within the delivery phase), during which a temperature equilibration between the medium and the pump head takes place. The correction dependence is determined by the control device, using the measurement data obtained, such that by superposing the normal time profile of the piston movement, i.e. the piston movement for generating the desired (constant) flow without taking into account the thermal equilibration effects, with the correction dependence, the piston or pistons of one or more of the piston-cylinder units, which are used to deliver the medium during the compensation phase, is or are controlled such that in the compensation phase drops in the flow or in the pressure are compensated or at least drastically reduced.

In general, the correction dependence can be determined for each (following) cycle of the piston pump unit, or only at particular time intervals or following triggering events, for example a change in the composition of the medium to be delivered.

According to embodiments that are easy to realize, the control arrangement determines the correction dependence $s_{corr}(t)$ such that the flow fluctuations caused by the compressibility of the medium or the flow fluctuations caused by the non-isothermal or adiabatic compression and the associated thermal equilibration processes are compensated by an addition of the correction dependence $s_{corr}(t)$ and the piston movement of the at least one of the at least two piston-cylinder units, which piston movement would bring about the desired flow without taking into account the compressibility of the medium.

Advantageously, in order to determine the correction dependence $s_{corr}(t)$, the control arrangement can use a predetermined, preferably analytical theoretical dependence $P_{theor}(t)$ for the time profile of the pressure and can determine one or more parameters of this dependence using the measurement data recorded during the measurement phase, such that the desired compensation effect, which is as optimal as possible, is achieved. The theoretical dependence $P_{theor}(t)$ can be stored in the control device as a functional analytical dependence or as a profile (which is, for example, standardized and can be influenced by one or more parameters) in the form of a table of values. The same also applies, of course, to the actual correction dependence $s_{corr}(t)$, the basic form of which does not have to be determined anew each time by the control device using the theoretical dependence (and optionally further constants or fixed temporal dependences). Rather, the control device is generally configured such that it determines merely the parameters of the correction dependence $s_{corr}(t)$.

Further improved accuracy can be achieved in that, during the determination of the correction dependence $s_{corr}(t)$, the control device takes into account the thermal equilibration occurring in the time period from the start of the measurement phase to the start of the compensation phase.

To this end, the control device can determine the correction dependence $s_{corr}(t)$ for the piston movement $s(t)$ using the relationship $$s_{corr}(t) = s_{corr\_theor}(t) - s_{corr\_theor}(t_5),$$

wherein $t_5$ denotes the time at which the compensation phase starts, and wherein the correction movement, necessary theoretically for compensating the thermal effect, of the work piston $s_{corr\_theor}(t)$ is determined using the relationship $$s_{corr\_theor}(t) = -Q_C \cdot \Delta P_{theor}(t),$$

wherein $Q_C$ denotes the compression coefficient $Q_C = \Delta s \Delta P$ in the region of the measurement phase, said compression coefficient resulting as the ratio of the change in pressure $\Delta P$ for an associated traveled distance $\Delta s$ of the piston in question, and wherein $\Delta P_{theor}(t)$ denotes the profile of the theoretical pressure difference which describes the thermal equilibration process and results from the profile of the theoretical dependence $P_{theor}(t)$ minus the value for the pressure $P_M$ at the time at which the measurement phase starts.

According to one embodiment of the invention, the control device can use the relationship $$P_{theor}(t) = P_e + (P_M - P_e) \cdot e^{-\frac{t-t_3}{\tau}},$$

with the parameters $P_e$ and $\tau$, as the analytical theoretical dependence for the profile to be expected of the pressure $P_{theor}(t)$, wherein $P_e$ denotes the pressure after the end of the thermal equilibration and $\tau$ denotes the time constant of the equilibration process, and wherein $P_M$ denotes the pressure at the time $t_3$ at which the measurement phase starts.

The control device can carry out the measurement phase during the compression phase and use the data recorded during the measurement phase for determining at least one parameter of a measurement dependence $P_{mess}(t)$ in such a way that the measurement dependence $P_{mess}(t)$ approximates the recorded measurements in the best possible manner. The control device can determine the parameters of the theoretical dependence $P_{theor}(t)$ from the parameters of the measurement dependence $P_{mess}(t)$ thus determined.

If the control device carries out the measurement phase shortly in time before the end of the compression phase, it can use the theoretical dependence $P_{theor}(t)$ as the measurement dependence $P_{mess}(t)$. In this case, the parameters determined for the measurement dependence can be used without conversion for the theoretical dependence $P_{theor}(t)$ and thus directly to determine the correction dependence $s_{corr}(t)$.

According to another embodiment, the control device can carry out the measurement phase during the decompression phase, preferably shortly in time before the end of the decompression phase, and use the data recorded during the measurement phase for determining the parameters of a measurement dependence $P_{mess}(t)$ in such a way that the measurement dependence $P_{mess}(t)$ approximates the recorded measurements in the best possible manner. The control device can then determine the parameters of the theoretical dependence $P_{theor}(t)$ from the parameters of the measurement dependence $P_{mess}(t)$. However, in this case, a conversion is regularly necessary for this purpose, since in the measurement phase the free volume is larger during the decompression than the free volume prior to the start of the compensation phase.

In this case, the control device can use the relationship $$P_{tmess}(t) = P_{MD} + (P_{eD} - P_{MD}) \cdot \left(1 - e^{-\frac{t-t_{21}}{\tau_D}}\right),$$

with the parameters $P_{eD}$ and $\tau_D$, as measurement dependence, wherein $P_{eD}$ denotes the pressure after the end of the thermal equilibration and $\tau_D$ denotes the time constant of the equilibration process in the decompression phase, and wherein $P_{MD}$ denotes the pressure at the time $t_{21}$ at which the measurement phase starts. The control device can determine the parameters of the correction dependence $s_{corr}$ from the pressure values $P_{MD}$ and $P_{eD}$ or the pressure difference $\Delta P = P_{eD} - P_{MD}$ and the time constant $\tau_D$.

In order to determine a conversion rule, during a time period in which the flow to be delivered by the piston pump unit and the composition of the medium to be delivered are substantially constant, the control device can both determine the parameters of the measurement dependence by way of a measurement in the compression phase and also determine the parameters in the decompression phase. By comparing parameters that correspond to one another, in each case a conversion rule, preferably a conversion factor, can then be determined in order to calculate the relevant parameter determined in the decompression phase into a parameter of the correction dependence.

Since the pressure profile during the measurement phase depends on the properties of the medium, in particular its compressibility, the control device also has to be supplied with this information in order to determine the correction dependence. To this end, during the compression phase, the control unit can record at least two measurements for the pressure in the volume of the first piston-cylinder unit at at least two piston positions or a measurement for a pressure difference $\Delta P$ for a traveled distance of the piston $\Delta s$, and determine therefrom a value for the compressibility or a value for the compression coefficient $Q_c = \Delta s \Delta P$, wherein the two measurements or the region of the pressure difference are selected such that they are in the region of the system pressure.

However, a value for the compressibility or the compression coefficient $Q_c$ for the medium to be delivered may also be known to the control device, for example filed in a memory, or be supplied to said control device by a superordinate unit.

The control device can then use the value determined by it for the compressibility or the compression coefficient $Q_c$ to determine the correction dependence.

According to a further embodiment, rather than keeping the piston position constant during the measurement phase, the pressure in the volume of the piston-cylinder unit in question is kept constant during the measurement phase. To this end, the control device must comprise or realize a pressure control loop. Instead of the time profile of the pressure, in this embodiment, the time profile of the piston position is detected, said profile being necessary in order to achieve a constant pressure. The correction dependence $s_{corr}$ is determined from these measurement data such that in the compensation phase pressure drops or flow drops are compensated or at least drastically reduced.

Of course, in this variant, too, the control arrangement can determine the correction dependence $s_{corr}(t)$ such that the flow fluctuations caused by the compressibility of the medium are compensated by an addition of the correction dependence $s_{corr}(t)$ and the piston movement of the at least one of the at least two piston-cylinder units, which piston movement would bring about the desired flow without taking into account the thermal equilibration processes.

Here, too, in order to determine the correction dependence $s_{corr}(t)$, the control arrangement uses a predetermined theoretical, preferably analytical dependence $s_{corr\_theor}(t)$ for the time profile of the piston position or the piston speed and determines one or more parameters of this dependence using the measurement data recorded during the measurement phase.

Of course, in this variant, too, during the determination of the correction dependence $s_{corr}(t)$, the control device can take into account the thermal equilibration occurring in the time period from the start of the measurement phase to the start of the compensation phase.

The control device then determines the correction dependence $s_{corr}(t)$ for the piston movement $s(t)$ using the relationship $$s_{corr}(t) = s_{corr\_theor}(t) - s_{corr\_theor}(t_5),$$

wherein $t_5$ denotes the time at which the compensation phase starts.

According to one embodiment, the control device can determine the correction movement, necessary theoretically for compensating the thermal effect, of the work piston $s_{corr\_theor}(t)$ using the relationship $$s_{corr\_theor}(t) = (s_M - s_e) \cdot e^{-\frac{t-t_3}{\tau}},$$

with the functional parameters $s_e$ and $\tau$, wherein $s_e$ denotes the piston position after the end of the thermal equilibration and $\tau$ denotes the time constant of the equilibration process, and wherein $s_m$ denotes the piston position at the time $t_3$ at which the measurement phase starts.

In an alternative, in which the control device carries out the measurement phase during the compression phase and uses the data recorded during the measurement phase for determining at least one parameter of a measurement dependence $s_{mess}(t)$ in such a way that the measurement dependence $s_{mess}(t)$ approximates the recorded measurements in the best possible manner, the control device can determine the parameters of the theoretical dependence $s_{corr\_theor}(t)$ from the parameters of the measurement dependence $s_{mess}(t)$.

In this case, the control device can carry out the measurement phase shortly in time before the end of the compression phase and use the theoretical dependence $s_{corr\_theor}(t)$ as the measurement dependence $s_{mess}(t)$. Since, in this case, the measured values are determined in a pressure range which is located in the region of the system pressure, it is possible to dispense with conversion of the determined parameters into corresponding parameters of the correction dependence.

Even when the pressure is kept constant during the measurement phase, the control device can in this case carry out the measurement phase during the decompression phase, preferably shortly in time before the end of the decompression phase, and use the data recorded during the measurement phase for determining the parameters of a measurement dependence $s_{mess}(t)$ in such a way that the measurement dependence $s_{mess}(t)$ approximates the recorded measurements in the best possible manner. The control device can then determine the parameters of the theoretical dependence $s_{corr\_theor}(t)$ or the parameters of the correction dependence $s_{corr}(t)$ from the parameters of the measurement dependence $s_{mess}(t)$.

In this alternative, in which the pressure is kept constant, the control device can use the relationship $$s_{tmess}(t) = s_{MD} + (s_{eD} - s_{MD}) \cdot \left(1 - e^{-\frac{t-t_{21}}{\tau_D}}\right),$$

with the parameters $s_{eD}$ and $\tau_D$, for the measurement dependence $s_{mess}(t)$ wherein $s_{eD}$ denotes the pressure after the end of the thermal equilibration and $\tau_D$ denotes the time constant of the equilibration process, and wherein $s_e$ denotes the pressure at the time $t_{21}$ at which the measurement phase starts. Since, here, the parameters $s_{eD}$ and $\tau_D$ were determined during the decompression phase, they have to be converted into corresponding parameters of the correction dependence $s_{corr}(t)$. In this case, in particular the pressure difference $\Delta s_D = s_{eD} - s_{MD}$ can be converted into the pressure difference $\Delta s = s_M - s_e$. The same applies for the time constants $\tau_D$ and $\tau$.

For this purpose, during a period in which the flow to be delivered by the piston pump unit and the composition of the medium to be delivered are substantially constant, the control device can both determine the parameters of the measurement dependence by way of a measurement in the compression phase and also determine the parameters in the decompression phase and, by comparing parameters that correspond to one another, determine in each case a conversion rule, preferably a conversion factor, in order to convert the relevant parameter determined in the decompression phase into a corresponding parameter of the correction dependence. This applies in particular when the parameters during the compression phase are determined here by performing a measurement in the vicinity of the system pressure.

According to another embodiment, the time constant $\tau$ or the time constant $\tau_D$ can be predetermined as a constant having a theoretically or empirically determined value and preferably be stored in the control device. The latter can then use the predetermined time constant in the determination of further parameters, in particular the particular final pressure $P_e$, $s_e$, $P_{eD}$, $s_{eD}$. This has the advantage that the measurement phase can then be selected to be considerably shorter, since in the extreme case, only two measurements, specifically at the start and at the end of the measurement phase, are enough to determine this parameter. Since these measurement points are relatively far apart in time, measurement errors and noise are included to a lesser extent in the measurement result.

Since the measurement is carried out in each case with non-moving medium and the compensation takes place in the compensation phase with moving medium, in order to take this difference into account, the control device can use, instead of the time constant $\tau$, an (optionally additionally) corrected, effective time constant $\tau_{eff}$, wherein the correction takes place such that the effective time constant $\tau_{eff}$ decreases with an increasing flow rate, wherein the control device determines the effective time constant $\tau_{eff}$ preferably in accordance with the relationship $$\tau_{eff} = \tau \cdot \left(1 - k \cdot \frac{Fl}{Fl_{max}}\right),$$

wherein Fl denotes the current flow rate and $Fl_{max}$ denotes the maximum possible flow rate, and wherein k denotes a constant factor between 0 and 1, which is determined by experiments or by simulation for the pump type in question.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

In HPLC pumps, the principle of the double piston pump has largely become established. In this case, for each pump, use is made of two pistons which can be moved either via a common drive, for example via a camshaft, or via individual drives. The piston movements are executed such that the sum of the flows delivered by the two pistons corresponds to the desired overall flow. In this case, a distinction is made between serial double piston pumps and parallel double piston pumps. The present invention can be applied to both pump types. Therefore, in the following text, both functional principles are briefly explained.

In gradient pumps, the mixing can already take place on the intake side, i.e. on the low-pressure side. In this case, only a single double piston pump is used to generate the gradient (LPG=low pressure gradient). However, the mixing can also take place on the high-pressure side (HPG=high pressure gradient) instead, wherein a separate double piston pump is used in this case for each solvent. Serial or parallel double piston pumps can be used both for LPG and for HPG.

The present application can be applied to all of these cases. However, a prerequisite for the application is that the double piston pumps have independent drives for each individual piston. In all of the following considerations, a single double piston pump of this type is always considered.

Both serial double piston pumps and parallel double piston pumps operate cyclically, i.e. a movement sequence that is substantially always the same repeats periodically, with the period duration being called the cycle time in the following text. An example of a serial double piston pump is found in EP 334 994 B1 or in U.S. Pat. No. 5,114,314 A.

The general functional principle of such serial double piston pumps according to the prior art is explained briefly in the following text with reference to FIG. 1.

The serial double piston pump 1 consists of a first piston-cylinder unit or working pump 10 and a second piston-cylinder unit or compensation pump 20. The working pump 10 consists of a working piston 12 which enters a working head 11 and is sealed off by means of a seal 16. The drive 15 can move the working piston via an actuating element 14, wherein the remaining free volume 13 in the working head depends on the particular piston position. This free volume is connected to an inlet valve 17 and an outlet valve 18 via connecting capillaries 19. In the simplest case, these valves are passive return valves, for example ball valves, which are arranged in FIG. 1 such that they allow only a throughflow from the bottom to the top. If the working piston 12 is withdrawn, i.e. moved toward the left in FIG. 1, the free volume 13 in the working head increases in size, the inlet valve 17 opens and fresh solvent is drawn in from a storage container (not illustrated) via the intake line 50. If the working piston 12 is moved forward, i.e. toward the right in FIG. 1, the free volume 13 decreases in size, the inlet valve 17 closes and the outlet valve 18 opens. The displaced volume is delivered by the connecting line 51 in the direction of the outlet.

The compensation pump 20 consists of a compensation head 21 having the compensation piston 22, seal 26, actuating element 24 and drive 25. While the working pump 10 is delivering solvent, the compensation piston 22 is withdrawn slowly so that the free volume 23 increases in size and a part of the flow delivered by the working pump 10 is stored in the compensation head 21. While the working pump 10 is drawing in new solvent and thus does not deliver a flow, the compensation piston 22 is moved back into the working head so that the volume 23 is continuously reduced in size and the displaced solvent maintains the flow at the outlet 52. The piston speeds are in this case selected such that the flow at the outlet 52 corresponds at any time to the desired value.

An example of a parallel double piston pump can be found in U.S. Pat. No. 4,137,011 A. The underlying principle of such parallel double piston pumps is intended to be explained by way of the schematic illustration in FIG. 2.

Figure 2:
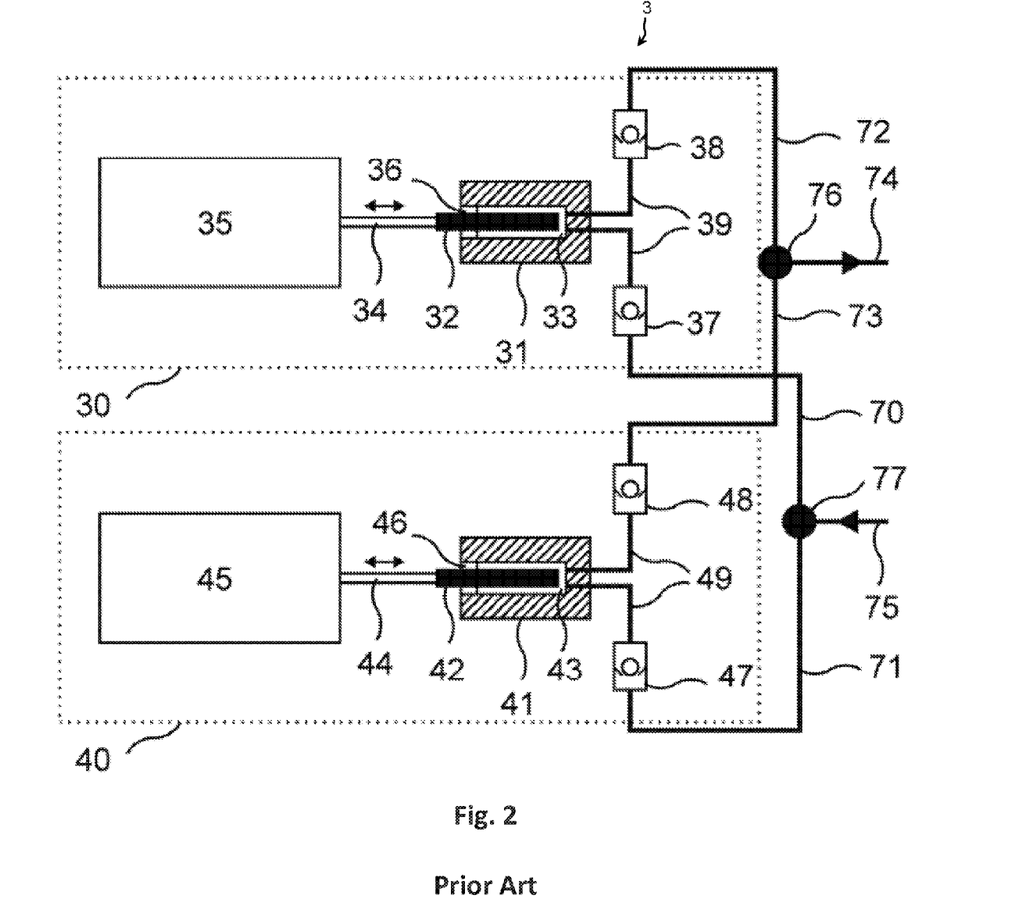
FIG. 2 shows a schematic illustration of a parallel double piston pump according to the prior art.

The parallel double piston pump 3 consists of two generally identical working pumps 30 and 40 which are each constructed in the same way as the working pump of the serial double piston pump. The components 31 to 39 and 41 to 49 correspond to the components 11 to 19 of the working pump 10 and are numbered analogously thereto.

The two working pump pistons 30, 40 alternately deliver the desired flow, i.e. while one working piston delivers the flow, the other draws in new solvent and vice versa. Inlets and outlets of the two pumps are each connected in parallel via the connecting capillaries 70 to 73 and the T-pieces 76 and 77, so that the two working pumps can draw in new solvent via a common intake line 75 and can make the delivered flow available at a common outlet 74.

Figure 1:
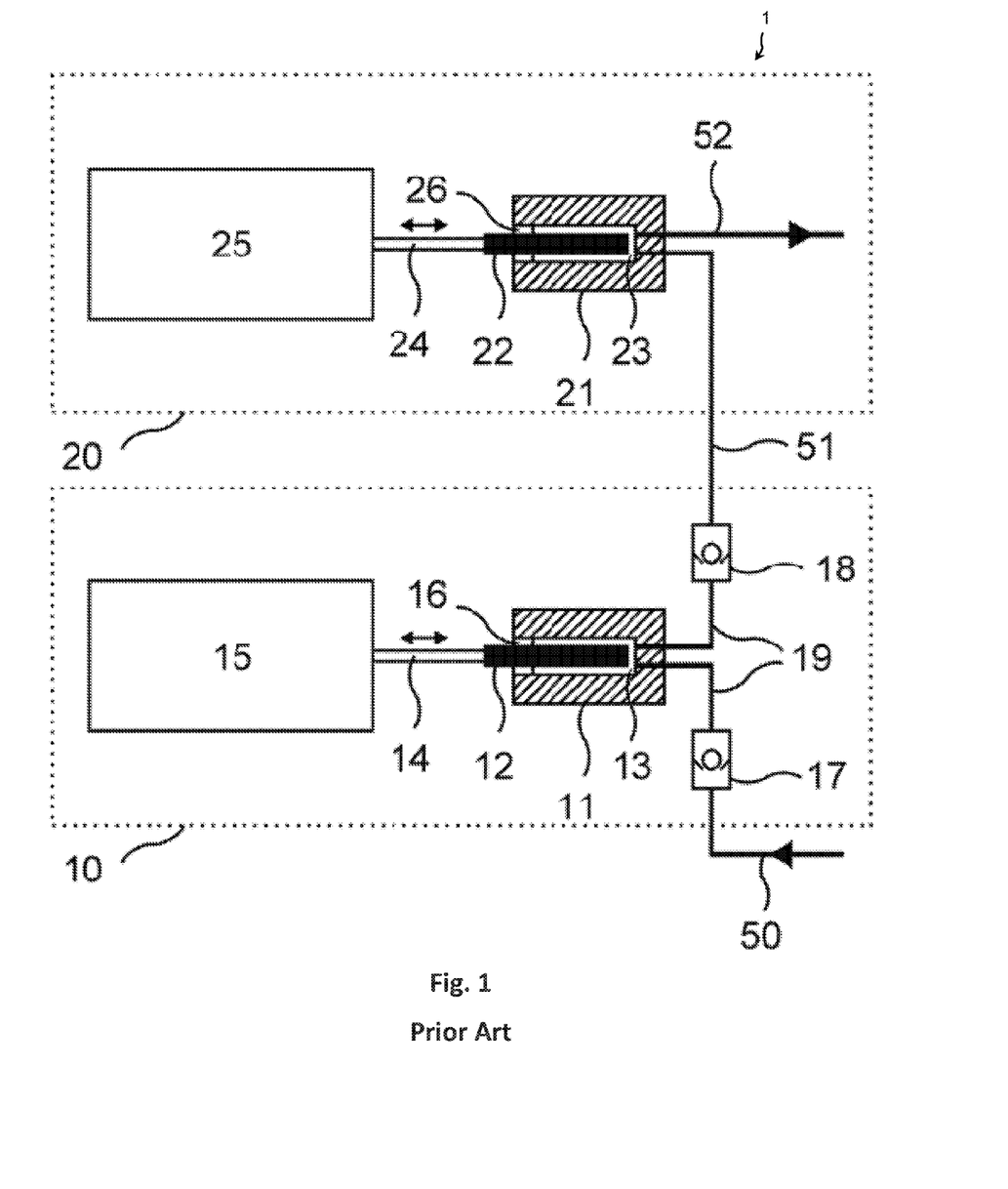
FIG. 1 shows a schematic illustration of a serial double piston pump according to the prior art.

Both a serial double piston pump according to FIG. 1 and also a parallel double piston pump according to FIG. 2 are capable, given appropriate control of the piston movement, of delivering a continuous flow that is largely free of pulsing at the outlet 52 and 74, respectively. On account of the flow resistance of the chromatographic separating column, a counter-pressure, which is also present at the pump outlet 52 and 74, respectively, and is designated system pressure in the following text, is produced in the medium to be delivered.

At higher operating pressures, the compressibility of the solvent becomes increasingly noticeable. In the following text, the processes which take place after a working pump has just drawn in new solvent are considered. The working pump in question is designated first working pump here, this meaning the (only) working pump in the case of a serial double piston pump and, in the case of a parallel double piston pump, meaning that working pump which has just drawn in new solvent at the time under consideration. The compensation pump or second working pump is designated other pump in the following text.

When the first working pump draws in new solvent, the solvent is initially pressureless in the working head, i.e. in the free volume 13 or 33 or 43, while the other pump maintains the system pressure at the pump outlet 52 and 74. Before the first working pump can deliver solvent in the direction of the pump outlet, the solvent first has to be compressed to the system pressure in order that the associated outlet valve 18 or 38 or 48 opens. This is known as compression and for this purpose the free volume 13 or 33 or 43 has to be reduced in size. This takes place by the first working piston 12 or 32 or 42 moving forward, with the travel that is necessary for compression depending on the system pressure and on the compressibility of the solvent in question. As soon as the compression is complete and the system pressure has been reached in the first working head, the associated outlet valve opens and the solvent displaced by the further piston movement is delivered in the direction of the outlet. The corresponding flow is added to the flow delivered by the other pump. Therefore, at this moment the piston speeds have to be changed such that an undesired change in the overall flow and thus also of the system pressure is avoided. This moment is known as transfer, since in this case the delivery of flow is transferred from the second pump to the first working pump. Following the transfer, the piston of the other pump is withdrawn in order to store or draw in solvent for the next stroke.

Depending on the construction of the pump, the transfer can take place suddenly or gradually. Similarly, the time at which the transfer starts can be determined in various ways.

There are various known technical solutions for this purpose. The present invention can be applied to all of these solutions.

The transfer is followed by the delivery phase in which the working pump in question delivers the flow.

During the compression phase, work is undertaken on the solvent, since the piston in question has to negotiate a travel counter to the pressure force. The compression work to be undertaken per pump cycle increases approximately quadratically with the system pressure and leads to heating of the solvent during the compression. On account of the thermal expansion of the solvent, the pressure rises more quickly above all in the upper pressure range than would actually be expected.

During the compression, the temperature of the working head 11 or 31 or 41 surrounding the solvent remains approximately constant, since the latter has a relatively large thermal capacity and the solvent cannot emit the compression heat as quickly as desired. As soon as the system pressure has been reached in the working head and the transfer begins, the pressure in the working head remains constant so that no further energy is supplied to the solvent. Now, a thermal equilibration process takes place, i.e. the solvent emits the compression heat as far as possible to the working head. The time constant of this equilibration process depends substantially on the thermal capacity and thermal conductivity of the solvent and of the working head.

As a result of the cooling, the liquid volume is decreased. Since the working pump is already involved in generating flow at this time, this contraction in volume is at the expense of the flow delivered at the outlet, i.e. the flow decreases for as long as the cooling process continues. This is noticeable in the cyclical operation of the pump as undesired periodic flow pulsing or pressure pulsing.

There are already a number of known approaches for reducing the problem of pulsing caused by thermal effects.

For example, U.S. Pat. No. 5,108,264 A (column 6, lines 31 et seq.) proposes calculating the thermal effect to be expected from the compressibility and the system pressure and to compensate it by corresponding piston movements, with a fixed time constant of 3 s being assumed for cooling. Such a calculation is possible when the properties of the solvent, in particular its specific thermal capacity and thermal conductivity, are known precisely and are always the same. However, this is not generally the case in HPLC pumps, which are intended to operate with different solvents. The properties of all solvents to be used would have to be determined in advance and stored in tables, this being associated with corresponding effort. Therefore, this method can be used only with major restrictions for universally usable HPLC pumps.

U.S. Pat. No. 5,108,264 A furthermore proposes (for example claim 4) measuring the system pressure prior to the transfer and controlling the piston movement by means of a control loop such that no drop in pressure occurs. A disadvantage with the use of such a pressure control loop is its susceptibility to faults by way of external influences. Specifically, drops or fluctuations in the system pressure can also be brought about for example by the switching of switching valves in the downstream further components of the chromatography system, by changes in the flow resistance of the chromatography column or by parallel-connected pumps in the case of an HPG pump. Such externally caused pressure fluctuations can result in erroneous behavior of control pressure loops. This could be avoided theoretically by using flow regulation instead of pressure regulation. However, this is technically considerably more difficult and more expensive to realize.

US 2008/0206067 A1 also deals with the same problems. Here, the use of control pressure loops is likewise proposed and this would lead to the above-described problem. As an alternative solution, it is proposed that the compression already be carried out some time before the transfer is due, so that the thermal effect has already abated. A disadvantage with this solution is that the abatement of the thermal effect, as mentioned in U.S. Pat. No. 5,108,264 A, lasts for about 3 seconds. However, in conventional HPLC pumps, at higher flow rates, the entire cycle time is only about one second. At least half of this is required for drawing in, compression and delivery. The remaining time is much too short to allow the thermal effects to abate sufficiently. Thus, the proposed method does not provide a usable solution precisely for high flow rates at which the drops in the flow are particularly critical on account of the usually high pressures and high compression speeds.

US 2010/0040483 A1 proposes avoiding the entire problem by separating the thermodynamic work of pressure generation from the precise flow generation. However, two pumps connected in series are necessary for this purpose, and this represents disadvantageously high complexity.

Similarly to in U.S. Pat. No. 5,108,264 A, WO 2006/103133 A1 also proposes calculating the thermal effects to be expected from the properties of the solvents in question and to compensate them by way of corresponding piston movements.

Proceeding from this prior art, the invention is based on the problem of creating a control arrangement for controlling a piston pump unit for liquid chromatography, in particular high-performance liquid chromatography, which makes it possible, in the case of a double piston pump—or more generally, in the case of a multiple piston pump—to substantially reduce or avoid the pulsing, brought about by the compression work and the associated thermal effects, in the flow without having to accept the disadvantages, explained above, of the known approaches. In particular, the solution according to the invention is intended to be adapted automatically to the properties of each particular solvent, it is not intended to be disrupted by externally caused pressure fluctuations and it is intended to function even at short cycle times.

The invention is based on the finding that the profile of the thermal effect can be predicted on account of a measurement which is carried out prior to the transfer, i.e. before the compensation phase in which the thermal equilibration between the medium and the environment occurs. On account of this predicted profile, it is possible to determine which piston movement will be necessary for correction purposes after the transfer.

The method according to the invention can be used to improve serial or parallel double piston pumps (or multiple piston pumps which have more than two piston-cylinder units) according to the prior art. A prerequisite for the application is merely that each working pump has a pressure measuring arrangement by way of which the pressure in the working head can be determined. In this case, it is not important whether the pressure is determined directly, i.e. with the aid of a pressure sensor, or indirectly by way of the forces or deformations exerted by the pressure.

Figure 3:
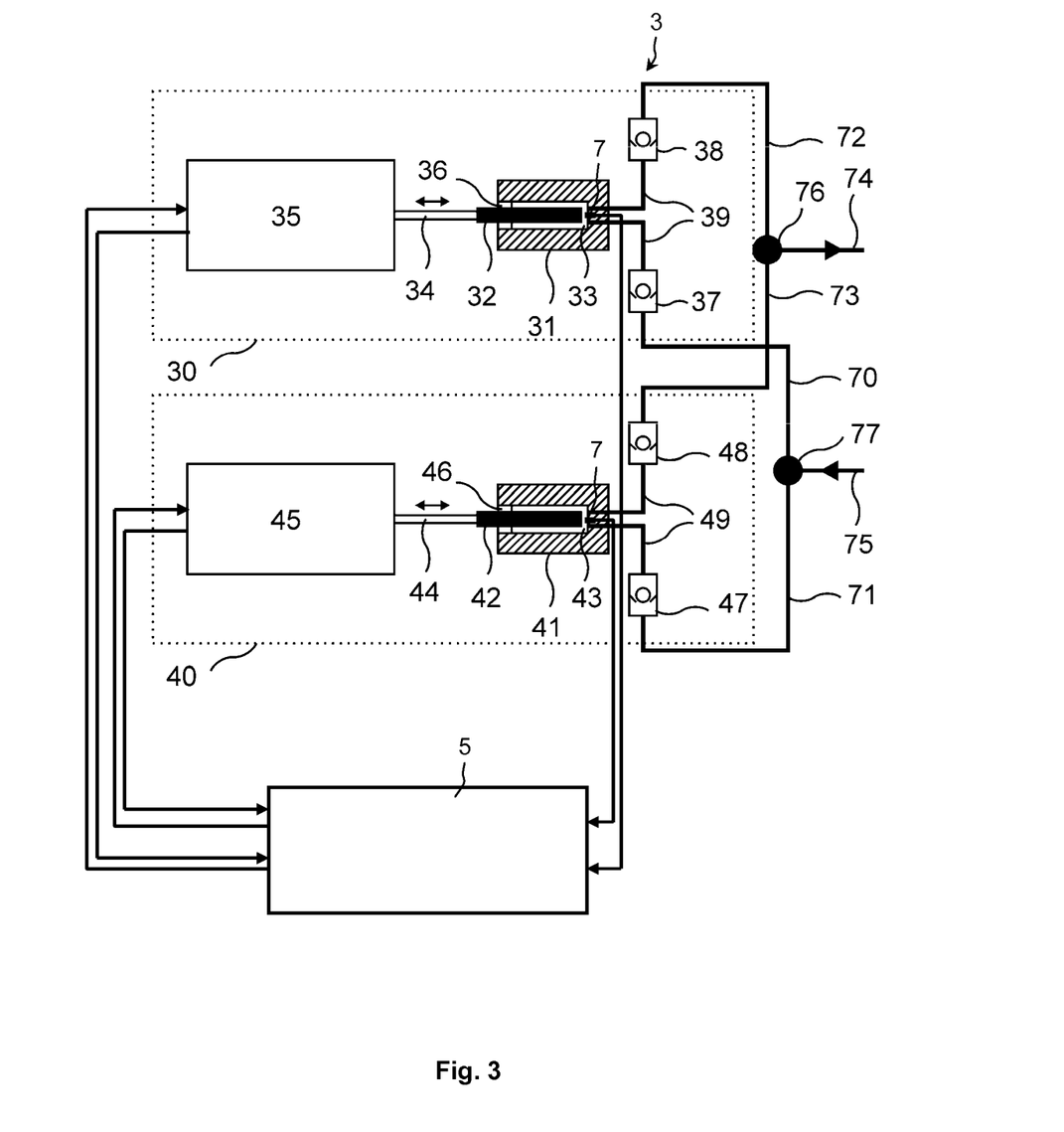
FIG. 3 shows a schematic illustration of a parallel double piston pump according to the invention.

The invention is described in the following text with reference to the embodiment in FIG. 3, which corresponds substantially to the known embodiment of a double piston pump 3, since the invention can be realized purely by way of a special control of the drive taking into account corresponding measurement signals or measurement and calculation results. Mutually corresponding components in FIGS. 2 and 3 are therefore provided with identical reference signs.

In a difference from FIG. 2, the double piston pump 3 has a control device 5 which controls the drives 35 and 35 of the two working pumps 30, 40, using the method described below. Provided in each piston-cylinder unit 31, 41 is a pressure sensor 7, the signal from which is supplied to the control unit 5. In addition, a device for recording the position of the pistons 32, 42 is provided and may be integrated into the respective drive 35, 45. Of course, said device can also be arranged directly on the piston-cylinder units 31, 41. The signals from these recording devices are likewise supplied to the control unit 5.

It is also possible for just one of the pumps 30, 40 to be equipped with corresponding sensors, in particular when the pumps are identical pumps having the same behavior, since then the in each case other pump can be controlled in a corresponding manner using the results obtained for the pump having sensor devices.

If the invention is applied to a serial double piston pump according to FIG. 1, then all that is necessary is for the working pump 10 to be provided with corresponding sensors.

The method according to the invention is explained in the following text with reference to the embodiment illustrated in FIG. 3 of a parallel double piston pump 3 by way of the diagrams illustrated in FIG. 4.

Figure 4:
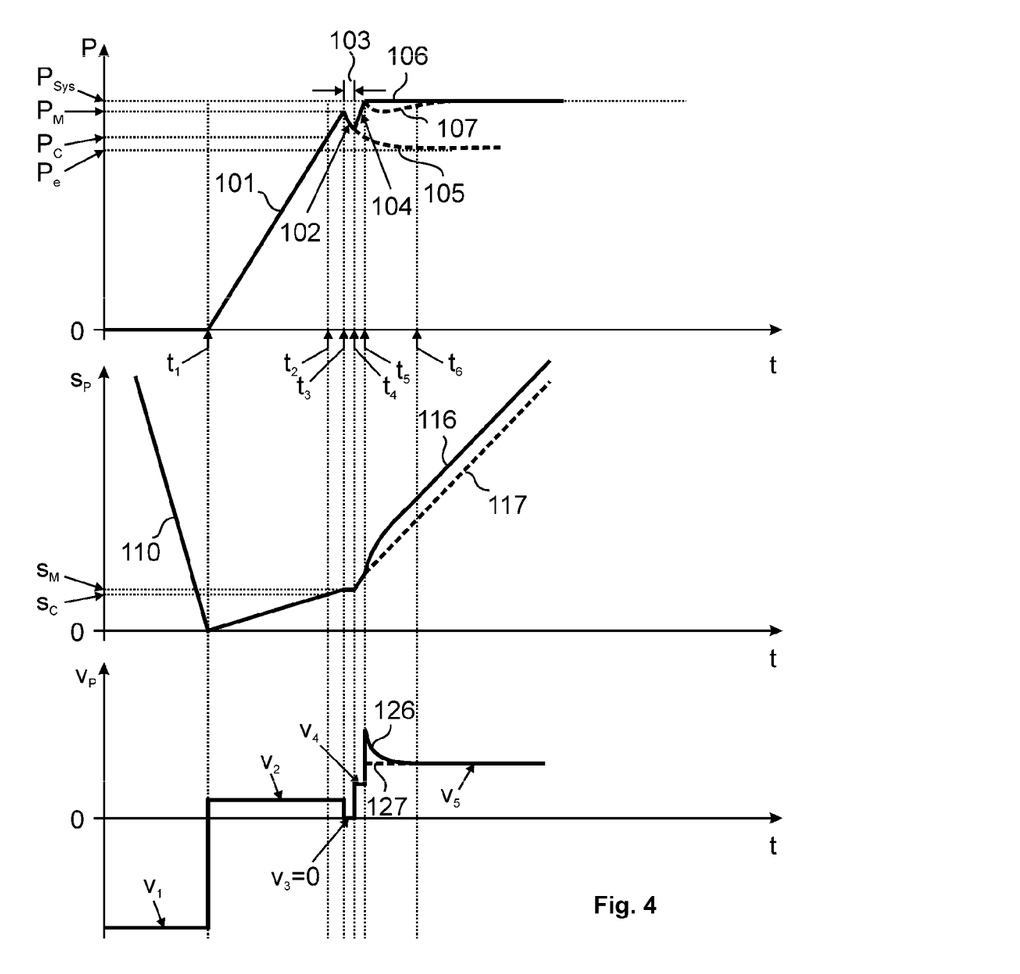
FIG. 4 shows diagrams for explaining the functioning of a first embodiment of a control arrangement according to the invention.

As can be seen from FIG. 4, the time axis is the same for all three diagrams and shows a section of the pumping cycle, specifically the compression phase, and also a certain period of time before and after. The pump, which is currently carrying out the compression, is denoted first working pump again, analogously to the above description. In the case of the parallel double piston pump according to FIG. 3, the processes shown take place alternately in the two working pumps 30, 40. The control device 5 in this case takes over all the necessary functions for controlling the drives 35, 45 and for recording and evaluating the signals from the pressure sensors 7 and the sensors integrated in the drives for recording the position of the pistons 32, 42.

The top diagram shows the profile of the pressure P(t) in the first piston-cylinder unit or the first working head 31, 41 over the time axis, wherein $P_{sys}$ represents the system pressure which is assumed in this example to be constant.

The middle diagram shows the position $s_P$ of the first working piston 32, 42 over the time axis, wherein in the zero position, the piston is completely withdrawn, i.e. entirely on the left-hand side in FIG. 3.

The bottom diagram shows the associated speed $v_P$ of the first working piston 32, 42. For the sake of simplification, instead of the real, ramp-like speed transitions, idealized, abrupt changes in speed are illustrated.

At the start, i.e. prior to the time $t_1$, the first working pump 30, 40 draws in new solvent. The pressure corresponds here to the ambient pressure. On account of the negative speed $v_1$ of the first working piston 32, 42 in this intake phase or filling phase, the piston position changes in the zero direction. This is illustrated by the curved section 110 of the middle diagram in FIG. 4. The zero point of the piston position $s_P=0$ corresponds to the rear reversal point of the piston 32, 42.

At the time $t_1$, the piston reaches its rear reversal point and now moves forward at the speed $v_2$. The solvent located in the working head is compressed, thereby leading to a pressure rise corresponding to the curve section 101 in the middle diagram in FIG. 4. This section up to the point at which the system pressure $P_{sys}$ is reached is denoted the compression phase. As a result of the work supplied during the compression, the medium to be delivered or the solvent is heated.

During the compression, the compressibility of the solvent, i.e. the relationship between the change in volume and the change in pressure, is measured. To this end, in each case when a first measured pressure $P_C$ and a second, higher measured pressure $P_M$ are reached, the associated piston positions $s_C$ and $s_M$ are stored (times $t_2$ and $t_3$). The compressibility can be calculated from the measurements (as described for example in U.S. Pat. No. 4,255,088 A). However, for the purpose of simplification, it is sufficient to calculate a compression quotient $Q_C$ which expresses the relationship between the change in distance and the change in pressure according to the following relationship:

$$Q_C = \frac{\Delta s}{\Delta P} = \frac{s_M - s_C}{P_M - P_C} \tag{1}$$

The measured pressures $P_M$ and $P_C$ are intended both to be located in the region of the system pressure and have to be selected such that, even in the case of inaccuracies in pressure recording, the actual measured pressure in no way reaches the system pressure, and that the differences in pressure and distance are sufficiently large in order to determine $Q_C$ precisely to a few percent.

When the second measured pressure $P_M$ is reached, i.e. shortly before the system pressure $P_{sys}$ would be reached, the movement of the working piston 12 or 32 or 42 and thus the compression continues to be stopped (at the time $t_3$). There then immediately follows a short measurement phase or measurement interval 103. During the measurement phase 103, the working piston is not moved further, i.e. the speed $v_3$ is zero in this phase.

During this measurement interval, no further energy is supplied to the previously compressed solvent, and the available volume remains constant. Since, on account of the compression heat, the solvent has a higher temperature than the surrounding working head, a thermal equilibration process starts, in which the solvent emits heat to the working head 31, 41. The resulting volume contraction results in a pressure drop 102 in the pressure profile, which is illustrated in the top diagram in FIG. 4. This time profile of the pressure P(t) is recorded by the control device 5 by means of the pressure sensors 7 thereof. To this end, the pressure P(t) in the working head is measured a number of times at time intervals during the duration of the measurement interval 103. This results in a measured pressure curve which reproduces the profile of the pressure drop 102 as a function of time. In reality, the sensors used for measurement exhibit a certain amount of noise. In order nevertheless to record the pressure curve with sufficient accuracy, the measurement interval therefore has to be selected to be sufficiently long. Expediently, the duration of the measurement interval should be between 0.1 s and 1 s, preferably at about 0.5 s.

If the piston 32, 42 were allowed to stand for a relatively long time in the position $s_M$, the thermal effect would gradually abate and the pressure drop would slow in accordance with the curve 105 in the top diagram in FIG. 4. This corresponds to the above-discussed solution according to the prior art, which is not applicable on account of the high time requirements at relatively high flow rates.

In the method according to the invention, in contrast to the prior art, there is no waiting until the thermal effect has largely abated, but rather the compression is continued at the time $t_4$ (the end of the measurement phase), until the system pressure $P_{sys}$ has been reached. This process is known as residual compression and starts immediately after the end of the short measurement interval 103, i.e. before the thermal effect has abated.

During the residual compression, the pressure in the working head rises in a manner corresponding to the curve 104 (see the top diagram in FIG. 4) and reaches the system pressure at the time $t_5$. At this time $t_5$, the relevant outlet valve 38, 48 opens and the transfer begins. As is known from the prior art, the speeds of one or both pistons 32, 42 now have to be adapted in a compensation phase, which represents the first part of the respective delivery phase of the pump, such that the overall flow does not change in an undesired manner.

On account of the short measurement phase 103, at this time $t_5$, the thermal effect has abated only a little, i.e. the medium to be delivered or solvent is still warmer than the surrounding working head 31, 41. The further temperature equilibration takes place during the compensation phase (i.e. during the transfer and the following delivery phase). The volume contraction resulting from the change in temperature reduces the flow delivered at the outlet 74 of the entire double piston pump 3. Without further measures, i.e. application of the movement profile 117 or the speed 127 (middle and bottom diagram, respectively, in FIG. 4), after the transfer has started, the flow delivered by the entire double piston pump and thus also the system pressure $P_{sys}$ drop in an undesired manner corresponding to the curve 107.

In order to avoid this, the volume contraction is calculated according to the invention from the time profile of the measured pressure curve 102 and compensated by a corresponding superposed piston movement $s_{corr}(t)$.

In order to calculate the volume contraction, consideration is given first of all to the conditions which would result if the piston continued to remain stationary after the measurement phase 103, i.e. starting at the time $t_4$. In this case, the curve 102 would continue and the pressure would thus follow the curve 105. This curve can be extrapolated relatively easily from the measured pressure curve 102, because the basic profile of such equilibration processes is known. To a first approximation, the equilibration process proceeds according to the following equation:

$$P_{theor}(t) = P_e + (P_M - P_e) \cdot e^{-\frac{t-t_3}{\tau}} \quad (2)$$

In this case, $P_e$ is the final pressure which would be reached theoretically after the equilibration process has fully abated, $P_M$ is the starting pressure at the time $t_3$ and $\tau$ is the time constant of the equilibration process (this can take for example about 3 s). This functional approach according to equation (2) is fit to the data recorded in the measurement interval 103, i.e. the unknown parameters $P_e$ and $\tau$ are optimized, for example with the aid of the method of least squares, such that the functional profile P(t) corresponds optimally to the measured data.

The function determined in this way corresponds to the theoretical pressure curve 105 which would result if the working piston continued to be stationary even after the time $t_4$.

If the thermal effect were not present, the pressure would already remain constant at $P=P_M$ starting at the time $t_3$.

Consequently, it is merely necessary to subtract $P_M$ from the right-hand part of equation (2) in order to obtain the (negative) theoretical change in pressure $\Delta P_{theor}(t)$ caused by the thermal effect:

$$\Delta P_{theor}(t) = P_e - P_M + (P_M - P_e) \cdot e^{-\frac{t-t_3}{\tau}} \quad (2)$$

The correction movement $s_{corr\_theor}(t)$ of the working piston, said correction movement $s_{corr\_theor}(t)$ theoretically corresponding to the profile of the change in pressure $\Delta P_{theor}(t)$ in order to compensate the thermal effect, can be calculated with the aid of the compression coefficient $Q_C$ to be determined according to equation (1):

$$s_{corr\_theor}(t) = -Q_C \cdot \Delta P_{theor} = -Q_C \cdot \left(P_e - P_M + (P_M - P_e) \cdot e^{-\frac{t-t_3}{\tau}}\right) \quad (4)$$

Although the above calculations relate to the conditions with the outlet valve 38, 48 closed, the volume contraction is independent of whether the outlet valve is open or closed. Therefore, the calculated correction movement can be applied even with the outlet valve 38, 48 open.

That part of the thermal effect which occurs before the start of the transfer, i.e. where $t<t_5$, is automatically compensated during the residual compression, since the pressure of the working pump is increased during the residual compression in any case up to the system pressure $P_{sys}$ or until the outlet valve 38, 48 opens.

Accordingly, starting from the time $t_5$, only the remaining correction dependence $s_{corr\_theor}(t)$ still has to be carried out. For the correction dependence corrected in this way, the relationship $$s_{corr}(t) = s_{corr\_theor}(t) - s_{corr\_theor}(t_5) \quad (5)$$

results, wherein the value $s_{corr\_theor}(t_5)$ is subtracted from equation (4). This therefore results overall in the following relationship for the correction dependence $s_{corr}(t)$:

$$s_{corr}(t) = \quad (6)$$
$$s_{corr\_theor}(t) - s_{corr\_theor}(t_5) = -Q_C \cdot (P_M - P_e) \cdot \left(e^{-\frac{t-t_3}{\tau}} - e^{-\frac{t_5-t_3}{\tau}}\right)$$

The working piston 32, 42 in question is displaced, in addition to the normal piston movement (curve 117 in the middle diagram in FIG. 4), by the distance $s_{corr}(t)$ calculated in this manner, thereby resulting in the curve 116. As a result, the free volume 33, 43 of the piston-cylinder unit 31, 41 in question is smaller than would be the case without correction, with the result that the volume contraction is compensated. Expressed in speeds, instead of the normal piston speed 127, first of all a higher piston speed as per curve 126 is traveled at, so that an additional flow is delivered to compensate the thermal effect. As a result, a pressure drop as per curve 107 is avoided and the pressure follows curve 106 (cf. the bottom diagram in FIG. 4).

In principle, a different measurement dependence $P_{mess}(t)$ could be used in the above variant in order to adapt to the measurements recorded in the measurement phase, and the parameters $P_e$ and $\tau$ of the theoretical correction dependence according to equation (4) or the correction dependence according to equation (6) could be calculated from said measurement dependence $P_{mess}(t)$, in particular the functional parameters thereof.

However, in the variant explained above, the theoretical dependence $P_{theor}(t)$ according to equation (2) was used as the measurement dependence $P_{mess}(t)$.

By implementing this method in the control device 5, the drop in flow or pressure, which would normally take place in the parallel double piston pump 3 on account of the compression heat during and after the transfer, can be completely compensated or at least drastically reduced. Of course, the same also applies for the case, not explicitly explained, of this procedure being used in a serial double piston pump according to FIG. 1.

In any case, in all of these variants, after the compression phase but before the start of the transfer, i.e. before the start of the delivery phase (or of the compensation phase), a short measurement phase is introduced in which the time pressure profile which results from the starting thermal equilibration process of the compression heat is measured, with the further, expected time profile of the volume contraction or a correction movement of the piston being calculated from this measured pressure profile, said correction movement being necessary to compensate this volume contraction.

If the measurement phase is carried out in a region in which the pressure corresponds approximately to the system pressure $P_{sys}$, then the influence of the residual compression and thus the influence of the energy supplied in the latter can be ignored. However it is also possible to carry out the measurement phase at a lower pressure (at which the compressibility of the medium is already taking effect) and to convert the parameters $P_e$ and $\tau$ which are measured at the lower pressures into the parameters which would result at pressure values in the region of the system pressure $P_{sys}$, taking into account a theoretically or empirically determined rule.

However, it is possible in principle to obtain all the information necessary for calculating the correction movements during the method by way of measurements. Therefore, the method can be adapted automatically to virtually any desired solvents. In contrast to known methods, in which the correction is calculated from already known physical properties of the solvents, in such a realization of the above-explained method, it is not necessary to enter the type of solvent currently being used or to determine or store the solvent properties separately. This is particularly advantageous in gradient pumps according to the LPG principle, in which the solvents are mixed at or upstream of the pump inlet in a variable composition, such that the properties of the mixture change depending on the respective mixing ratio. The method according to the invention automatically determines the optimum correction movement for the current mixing ratio. In some solutions according to the prior art, the physical properties for each mixing ratio that occurs have to be known, this requiring a very large amount of effort.

A further advantage of this method is that it operates independently of changes in the system pressure. Even if a change in system pressure takes place during the short measurement phase, this does not disrupt the measurement since the relevant outlet valve is still closed during the measurement. While the correction is being carried out, changes in the system pressure likewise have no disruptive influence since the correction takes place independently of the pressure, purely volumetrically by way of piston movements calculated in advance. In contrast thereto, pressure control loops, as are proposed in a number of the known approaches, can be disruptively influenced by changes in the system pressure, and this results in erroneous correction.

A further important advantage of the method is that it is applicable even at high flow rates or short cycle times, since the measurement process requires only a little time and the correction is superposed on the normal piston movement without an additional time requirement. It is not necessary to wait until the thermal effect has largely abated, which would result in restrictions with regard to the maximum flow rate.

Beyond the abovementioned specific advantages, the invention provides the same advantages as the known solutions according to the prior art: even at high working pressures and highly compressible solvents, drops in flow or pressure, which are caused by the compression heat being emitted to the pump head, are virtually completely eliminated.

In the following text, variants of the basic method are described, the abovementioned advantages likewise applying to said variants.

In the above explanation, advantageously the measured pressure $P_M$ at which the measurement phase 103 starts is selected to be the same as the upper measured pressure for determining the compressibility or the compression quotient $Q_C$. In other words: the measurement phase for determining the correction dependence $s_{corr}(t)$ immediately follows the phase of measuring the pressure values for determining the compression quotient. Although this is expedient, it is not absolutely necessary. The two measurements merely have to take place approximately in the same pressure range. The compression quotient can, for example, also be determined at somewhat lower pressures.

In principle, of course, the compression quotient or a value for the compressibility can also be predetermined for the relevant medium to be delivered, and be stored in the control device 5. However, this variant loses the advantage that the method is adapted automatically to the medium to be delivered.

In all of the variants discussed above and below, the correction movement $s_{corr}(t)$ does not absolutely have to be carried out with the relevant working piston, but rather the correction can be carried out, in the case of a serial pump, also with the compensation piston 22 or, in the case of a parallel pump, also with the second working piston 32, 42, as long as the outlet valve thereof is open. It is likewise possible to divide the correction movement between both pistons. In this case, the sum of the correction movements has to be identical to the determined correction movement $s_{corr}(t)$.

The simplest, and therefore preferred, embodiment is still, however, carrying out the correction by way of the working piston which has previously compressed the medium.

In a further variant of the method, a pressure control loop can control the movement of the working piston during the measurement interval 103 such that the pressure of the working pump remains constant for the duration of the measurement interval. Then, rather than the time profile of the pressure signal, the time profile of the relevant piston position is recorded and evaluated as the measurement signal. Of course, for this purpose, the control device necessarily has to be designed such that the piston position can be recorded sufficiently precisely. However, this does not necessarily mean that a separate arrangement has to be provided for recording purposes. Since the piston positions and speeds are predetermined by the same control arrangement, it may be quite sufficient to use these default values. In many drive systems, it is then possible to proceed from the assumption that the actual mechanical piston position corresponds sufficiently accurately with the default value.

The procedure is similar to the above-described procedure. Since, however, the piston position data recorded during the measurement interval 103 directly represents the correction function here, the term $-Q_C$ is dispensed with in equation (4) and the correction dependence $s_{corr}(t)$, for which the parameters $s_e$ and $\tau$ are intended to be determined, is:

$$s_{corr}(t) = (s_M - s_e) \cdot \left(e^{-\frac{t-t_3}{\tau}} - e^{-\frac{t_5-t_3}{\tau}}\right) \quad (7)$$

wherein, in order to describe the correction movement theoretically necessary to compensate the thermal effect, the relationship $$s_{corr\_theor}(t) = (s_M - s_e) \cdot e^{-\frac{t-t_3}{\tau}} \quad (8)$$

was used here. The unknown parameters $s_e$ and $\tau$ are determined analogously to the already described procedure, using a measurement function $s_{mess}(t)$. In the simplest case, it is again possible to use the relationship according to equation (7) as the measurement function $s_{mess}(t)$ when the measurement is carried out in the region of the system pressure $P_{sys}$. In this case, the following thus applies:

$$s_{mess}(t) = s_{corr\_theor}(t) = (s_M - s_e) \cdot e^{-\frac{t-t_3}{\tau}} \quad (9)$$

However, in principle, it is again also possible here to use some other dependence as the measurement dependence and to determine the parameters of the correction dependence according to equation (7) from the course thereof or the functional parameters thereof.

In contrast to the pressure control loops proposed in the prior art, here it is not the system pressure that is controlled but rather the pressure of the working pump during the measurement interval. Since, at this time, the associated outlet valve is still closed, the pressure control loop is not influenced by any changes in the system pressure.

As described above, the measurement interval 103 (or the corresponding measurement interval during the determination of the profile of the piston position at a constantly controlled pressure) has to have a certain minimum duration in order that the measured pressure curve can be determined sufficiently precisely. The requirements placed on the accuracy of the measurement can be greatly reduced if the time constant $\tau$ is assumed to be fixed. Then, the only variable parameter in the equations is the final pressure $P_e$ or the final position $s_e$. In order to determine these parameters, two measurement points at the start and the end of the measurement interval are sufficient. Since these two measurement points are located relatively far apart in time, noise is included less strongly in the result of the calculation. Conversely, in this way, a sufficiently precise result is still achieved even in the case of a relatively short measurement interval. Such shortening of the measurement interval is of interest when the cycle time of the pump is short, i.e. above all at high flow rates.

Hitherto, in the above variants, the fact that the relevant working piston 32, 42 delivers solvents located in the working head starting from the transfer and is thus set into movement, has not been discussed. As a result, the heat exchange between the medium and the surrounding components is improved and so the solvent cools more rapidly than if it is at a standstill. Thus, the volume contraction takes place more quickly.

Therefore, the piston movement also has to be carried out more quickly to compensate the thermal effect. This can be achieved according to the invention in that the time constant $\tau$ of the compensation movement is multiplied by a variable factor which becomes less with increasing pump flow. At a low flow, i.e. when virtually no piston movement takes place during the thermal effect, this factor is approximately 1, i.e. the correction is carried out with the calculated time constant. At a higher flow, the factor becomes smaller, and so the time constant applied is shortened in a corresponding manner.

The function according to which the factor has to be calculated depends on the geometry of the fluid components of the pump. However, in practice, for example the following simple approach, in which the factor decreases linearly with increasing flow, suffices:

$$\tau_{eff} = \tau_{calc} \cdot \left(1 - k \cdot \frac{Fl}{Fl_{max}}\right) \quad (10)$$

In this case, $\tau_{eff}$ denotes the calculated time constant which is used instead of $\tau$ in equation (6) and equation (7) for calculating the correction movement. $\tau_{calc}$ is the calculated time constant which was determined by fitting the respective measurement dependence $P_{mess}(t)$ or $s_{mess}(t)$ to the curve 102 (in the event that the measurement dependence is selected to be the same as the theoretical correction dependence $P_{theor}(t)$ or $s_{theor}(t)$), k is a factor to be defined between 0 and 1, Fl is the set flow in the double piston pump in question, and $Fl_{max}$ is the maximum possible flow in the pump.

$\tau_{eff} = \tau_{calc}$ at flow=0. $\tau_{eff}$ decreases linearly as the flow rises. $\tau_{eff} = 0.2\tau_{calc}$ at k=0.8 and maximum flow.

The factor k can be optimized easily by way of experiments for a particular pump type. To this end, the pump is operated at high pressure and medium to high flow and the value of k is varied such that an optimum pulsing behavior results.

In the above-described embodiments, the thermal effect is recorded in the measurement interval 103 preferably shortly before the transfer which starts at the time $t_5$. In this case, it is necessary always to ensure that the transfer is ended in good time before the other pump has reached the end of its delivery travel. If the set flow of the double piston pump 3 increases during the measurement interval 103 or shortly before the latter, the other pump reaches the end of its delivery travel earlier than originally assumed and so the available measurement time is suddenly greatly reduced.

This problem can be avoided by way of the alternative embodiment described in the following text. This variant is based on the fact that, in pumps of the type described, the free volume 13 or 33 or 43 (FIG. 1 or 2 and 3) in the relevant working head is also not 0 when the piston is in its front end position, on account of unavoidable dead volumes. The free residual volume that then remains is then under the system pressure $P_{sys}$ at the end of the transfer. If the piston is then withdrawn in order to draw in new solvent, this residual volume is initially decompressed until the pressure in the working head reaches ambient pressure and new solvent is drawn in.

During this decompression, a thermal effect likewise takes place since the solvent cools on account of the expansion and the pressure therefore reduces more quickly than would be expected on account of the piston movement. This thermal effect proceeds inversely compared with during the compression and can be recorded in an analogous way according to the invention.

Figure 5:
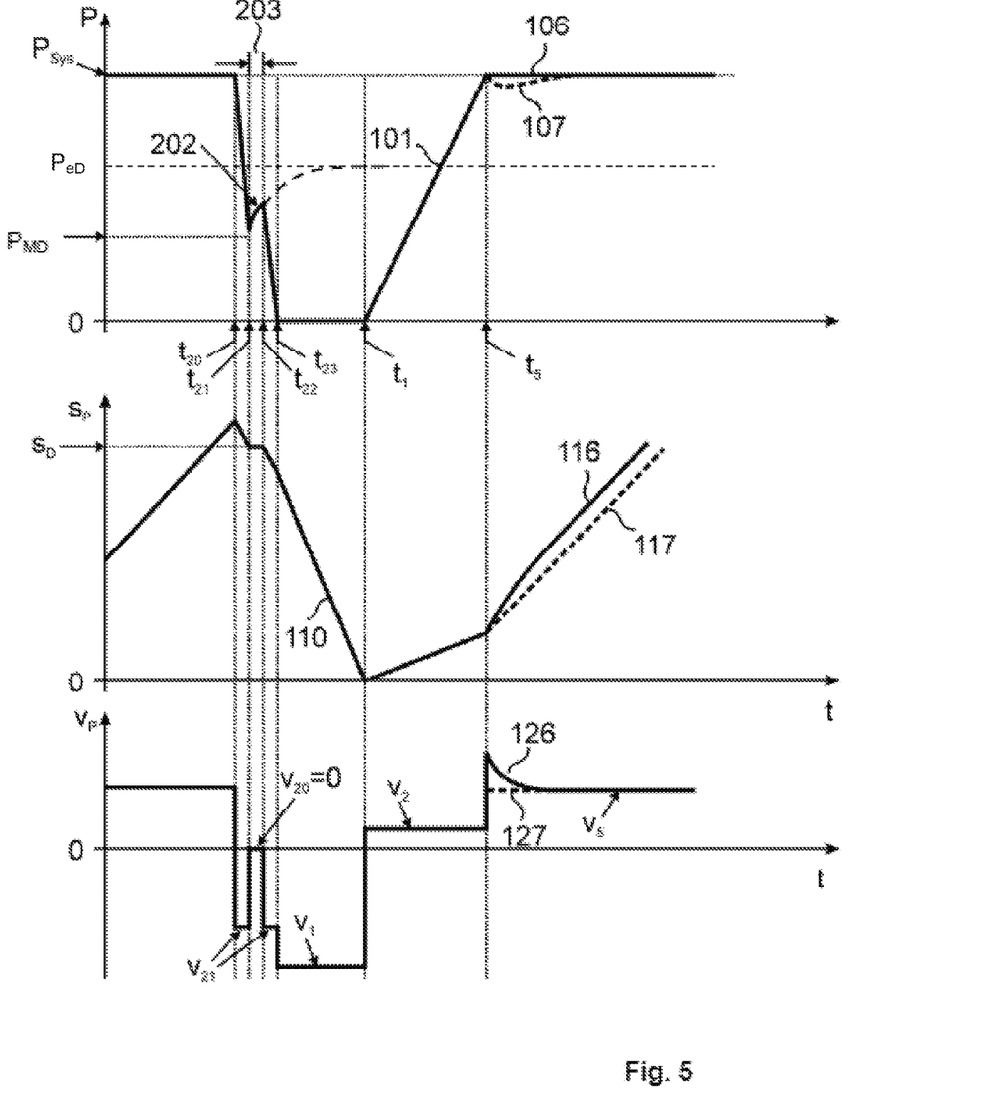
FIG. 5 shows diagrams for explaining the functioning of a further embodiment of a control arrangement according to the invention.

FIG. 5 shows, in a similar manner to FIG. 4, the pressure P, the piston position $s_P$ and the speed $v_P$ of the working piston. At the start, the working piston delivers solvent and reaches its front end position at the time $t_{20}$. Now, the piston is withdrawn at the speed $v_{21}$. As a result, more space is available to the remaining free residual volume and the pressure rapidly drops. This process is known as decompression in the following text.

The decompression is interrupted at the time $t_{21}$ or when the pressure $P_{MD}$ is reached, i.e. the piston is stopped ($v_{20}=0$). With that, the measurement interval 203 starts. In an analogous manner to the above-described processes, a thermal equilibration process takes place during the measurement interval, with the previously cooled solvent being heated during said thermal equilibration process. This results in a pressure rise as per curve 202, which is recorded by measurement. Starting from the time $t_{22}$, the remaining decompression is carried out, i.e. the piston is withdrawn further. At the time $t_{23}$, the ambient pressure is reached, the inlet valve 17 or 37 or 47 is opened and the drawing-in phase 110 starts, with new solvent being drawn in during said phase 110. At the time $t_1$, the piston reaches its rear end position. This is followed by the compression 101, in which the piston moves forward at the speed $v_2$. At the end of the compression, i.e. starting from the time $t_5$, the compression heat is emitted, as described above, resulting in a volume contraction which, without further measures, would result in a pressure drop 107.

In this embodiment, the time profile of this volume contraction is estimated from the data obtained during the measurement interval 203 and is compensated in the same way as described above, in that, instead of the piston movement 117, a corrected piston movement 116 is carried out.

Since, in this variant of the invention, the thermal effect is only measured during the decompression and thus in the region of the front end position of the piston, the effective liquid volume is much smaller than the liquid volume at the end of the compression. Furthermore, the majority of this liquid volume is located in a narrow region between the piston and the pump head. Therefore, the thermal contact between the liquid and the pump head is considerably better than when the piston is located further toward the rear. As a result of both, the time constant $\tau_D$ of this thermal equilibration process is considerably shorter than the time constant $\tau$ which is effective in the compression phase or toward the end of the compression phase. Therefore, a considerably shorter measurement interval 203 is sufficient to record the equilibration process than in the above-described method with measurement at the end of the compression phase.

In this embodiment, the relationship can thus be used as the measurement dependence, wherein $\tau_D$ denotes the time constant of this exponentially proceeding measurement dependence $P_{mess}(t)$ $P_{eD}$ denotes the final pressure which would be established at the end of the thermal equilibration (if the measurement phase had been selected to be correspondingly long), and $P_{MD}$ denotes the measured pressure at the start of the measurement phase 203.

The conversion factor between the time constant $\tau_D$ determined during the measurement interval 203 and the time constant $\tau$ required for correction, and also between the pressure difference $\Delta P_D = P_{eD} - P_{MD}$ determined during the measurement interval 203 and the pressure difference $\Delta P = P_e - P_M$ required for correction, can be determined empirically in a pilot test. In this case, the measurement is carried out both during the decompression in the measurement interval 203 and also at the end of the compression in the measurement interval 103, and a conversion factor between $\tau$ and $\tau_D$ or between $\Delta P$ and $\Delta P_D$ is determined. This pilot test can also take place in a fully automated manner if no change in flow is currently to be expected.

However, in practice it is generally sufficient to use the empirically determined values directly for both time constants $\tau$ and $\tau_D$ without conversion and to calculate the corrected piston movement 116 therefrom. This is because, in many cases, it will be possible to assume that the time constants in normal operation are identical to those during a pilot test. In other words, during normal operation, the time constant $\tau_D$ determined during the pilot test is used for measurement after the decompression, instead of determining the time constant again from the measurements. Similarly, in order to calculate the compensation movement, the time constant $\tau$ determined during the pilot test is used directly without calculating this by conversion of $\tau_D$.

In order to create largely identical conditions during the measurement in the decompression phase to those at the end of the compression phase, it is favorable for the initial pressure of the measurement $P_{MD}$ to be virtually identical to the ambient pressure and for the decompression to be carried out as quickly as possible. In this case, $P_{MD}$ must not be selected to be identical to the ambient pressure, since otherwise already small inaccuracies of the pressure sensors 7 could result in new solvent being drawn in prior to the measurement. However, $P_{MD}$ can also be selected to be considerably higher than ambient pressure, wherein, in this case, the measurement result has to be converted in a manner corresponding to the lower pressure difference.

This embodiment makes it possible to carry out the measurement in a non-critical time interval and to manage with a shorter measurement duration. If the pump flow delivered increases during the measurement, the shortening of the overall time that is available can be reduced without a problem by a higher drawing-in speed or more rapid compression. Thus, in this case, the entire measurement duration that is required is available.

Of course, it is also possible in this variant to constantly control the pressure and to record the piston position as measurement variable instead of keeping the piston position constant and recording the pressure profile in the measurement phase.

Analogously to the above-explained embodiments, the relationship $$P_{tmess}(t) = P_{MD} + (P_{eD} - P_{MD}) \cdot \left(1 - e^{-\frac{t-t_{21}}{\tau_D}}\right) \quad (11)$$

$$s_{tmess}(t) = s_{MD} + (s_{eD} - s_{MD}) \cdot \left(1 - e^{-\frac{t-t_{21}}{\tau_D}}\right) \quad (12)$$

can be used here as measurement dependence. The conversion factor between the time constant $\tau_D$ determined during the decompression phase and the time constant $\tau$ required for correction, and also between the difference in distance $\Delta s = s_{eD} - s_{MD}$ determined during the decompression phase and the difference in pressure $\Delta s = s_e - s_m$ required for correction can be determined, as described above, in a pilot test.

Finally, it should be noted that, of course, all of the above-explained variants can be combined with one another, insofar as this is sensible, and the variants are not mutually exclusive.

What is claimed is:

1. A piston pump unit for liquid chromatography comprising:
   (a) at least two piston-cylinder units configured to generate, at an outlet port, a predetermined flow of a liquid medium at a system pressure, in which each piston-cylinder unit has an independent drive device,
   (b) a control device configured to
      (i) control the independent drive devices for the at least two piston-cylinder units,
      (ii) compress the liquid medium in a first cylinder of the at least two piston-cylinder units in a compression phase from a starting pressure to the system pressure,
      (iii) decompress the first cylinder of the at least two piston-cylinder units in a decompression phase,
      (iv) record pressure values as a function of time in a cylinder volume of at least a first of the at least two piston-cylinder units during a measurement phase,
      (v) stop the independent drive device for the first piston-cylinder unit for a predetermined time period during the measurement phase, the measurement phase being either a measurement phase of the compression phase of the first piston-cylinder unit or a measurement phase of the decompression phase of the first piston-cylinder unit;
      (vi) determine a correction dependence to correct a piston movement of at least one of the at least two piston-cylinder units during a compensation phase based on the recorded pressure values as a function of time, and
      (vii) control the at least one of the at least two piston-cylinder units using the correction dependence during the compensation phase.

2. The piston pump unit of claim 1, in which the at least two piston-cylinder units are further configured to operate cyclically in a phase-offset manner.

3. The piston pump unit of claim 1. further comprising: a pressure sensor configured to measure the pressure values in the cylinder volume of at least a first of the at least two piston-cylinder units.

4. The piston pump unit of claim 1, in which the correction dependence is further based on a compression coefficient, a pressure value and a time value when the compressing or decompressing of the first cylinder is stopped, and another time value at a start of the compensation phase.

5. The piston pump unit of claim 4, in which the compression coefficient is a ratio of a change in pressure values to an associated travel distance of a piston in the first cylinder of the at least two piston-cylinder units.

6. The piston pump unit of claim 5, in which the control device is further configured to
   (vii) calculate the compression coefficient using a compression coefficient equation, the compression coefficient equation comprising:

$$Q_c = \Delta s / \Delta P,$$

where $Q_c$ is the compression coefficient, and $\Delta P$ is the change in the pressure values for the associated travel distance $\Delta s$ of the piston in the first cylinder of the at least two piston-cylinder units.

7. The piston pump unit of claim 6, in which the control device is further configured to
   (viii) calculate the correction dependence using a correction dependence equation for piston movement, the correction dependence equation for piston movement comprising:

$$s_{corr}(t) = -Q_C \cdot (P_M - P_e) \cdot \left( e^{-\frac{t-t_3}{\tau}} - e^{-\frac{t_5-t_3}{\tau}} \right),$$

where $s_{corr}(t)$ is the correction dependence, t is a time value, $Q_c$ is the compression coefficient, $P_M$ is a pressure at a time $t_3$ in which the measurement phase starts, $t_5$ is a time in which the compensation phase starts, and $P_e$ and $\tau$ are both parameters.

8. The piston pump unit of claim 1, in which the control device is further configured to calculate parameters $P_{eD}$ and $\tau D$ of the correction dependence, where the measurement phase occurs during the decompression phase, using a pressure measurement equation and the recorded pressure values as a function of time, the pressure measurement equation comprising:

$$P_{tmess}(t) = P_{MD} + (P_{eD} - P_{MD}) \cdot \left( 1 - e^{-\frac{t-t_{21}}{\tau_D}} \right)$$

where $P_{tmess}(t)$ is the recorded pressure values as a function of time, t is a time value, $P_{MD}$ is a pressure at a time $t_{21}$ in which the measurement phase starts.

9. The piston pump unit of claim 8, in which the control device is further configured to
   (viii) calculate the correction dependence using a correction dependence equation for piston movement, the correction dependence equation for piston movement comprising:

$$s_{corr}(t) = -Q_c \cdot (P_M - P_e) \cdot \left( e^{-\frac{t-t_3}{\tau}} - e^{-\frac{t_5-t_3}{\tau}} \right),$$

where $s_{corr}(t)$ is the correction dependence, t is a time value, $Q_C$, is the compression coefficient, $P_M$ is a pressure at a time $t_3$ in which the measurement phase starts, $t_5$ is a time in which the compensation phase starts, and $P_e$ and $\tau$ are both parameters,
   in which the control device is further configured to convert the parameter $P_{eD}$ of the decompression phase to the parameter $P_e$ of the correction dependence based on a first conversion factor, and to convert the parameter $\tau_D$ of the decompression phase to the parameter $\tau$ of the correction dependence based on a second conversion factor.

10. The piston pump unit of claim 7, in which the control device is further configured to calculate an effective time constant for the parameter $\tau$ using an effective time constant equation, the effective time constant equation comprising:

$$\text{effective time constant} = \tau \cdot \left( 1 - k \cdot \frac{Fl}{Fl_{max}} \right)$$

where Fl is a current flow rate, $Fl_{max}$ is a maximum flow rate, and k is a constant factor between 0 and 1; and to input the calculated effective time constant into the correction dependence for the parameter τ.

11. A piston pump unit for liquid chromatography comprising:
(a) at least two piston-cylinder units configured to generate, at an outlet port, a predetermined flow of a liquid medium at a system pressure, in which each piston-cylinder unit has an independent drive device,
(b) a control device configured to
(i) control the independent drive devices for the at least two piston-cylinder units,
(ii) compress the liquid medium in a first cylinder of the at least two piston-cylinder units in a compression phase from a starting pressure to the system pressure,
(iii) decompress the first cylinder of the at least two piston-cylinder units in a decompression phase,
(iv) record piston positions or piston speeds as a function of time in a cylinder volume of at least a first of the at least two piston-cylinder units during a measurement phase,
(v) maintain a constant pressure in the cylinder volume of the first piston-cylinder unit for a predetermined time period during the measurement phase, the measurement phase being either a measurement phase of the compression phase of the first piston-cylinder unit or a measurement phase of the decompression phase of the first piston-cylinder unit;
(vi) determine a correction dependence to correct a piston movement of at least one of the at least two piston-cylinder units during a compensation phase based on the recorded piston positions or the recorded piston speeds as a function of time, and
(vii) control the at least one of the at least two piston-cylinder units using the correction dependence during the compensation phase.

12. The piston pump unit of claim 11, in which the control device is further configured to calculate parameters $s_e$ and τ of the correction dependence using a piston position equation and the recorded piston positions or the recorded piston speeds as a function of time, the piston position equation comprising:

$$s_{mess}(t) = (s_M - s_e) \cdot e^{-\frac{t-t_3}{\tau}}$$

where $S_{mess}(t)$ is the recorded piston positions as a function of time, t is a time value, $s_M$ is a position of the piston at a time $t_3$ in which the measurement phase starts.

13. The piston pump unit of claim 12, in which the control device is further configured to calculate an effective time constant for the parameter τ using an effective time constant equation, the effective time constant equation comprising:

$$\text{effective time constant} = \tau \cdot \left(1 - k \cdot \frac{Fl}{Fl_{max}}\right)$$

where Fl is a current flow rate, $Fl_{max}$ is a maximum flow rate, and k is a constant factor between 0 and 1, and to input the calculated effective time constant into the correction dependence for the parameter τ.

14. A method of pumping a liquid with a piston-pump unit for liquid chromatography, the method comprising:
decompressing a first cylinder of at least two piston-cylinder units during a decompression phase, in which a volume of the first cylinder increases;
compressing the liquid in the first cylinder of the at least two piston-cylinder units during a compression phase, in which a pressure of the liquid changes from a starting pressure to a system pressure;
measuring pressure values in the volume of the first cylinder as a function of time during a measurement phase of either the compression phase or the decompression phase;
during the measurement phase, stopping the compressing or the decompressing of the first cylinder for a predetermined time period;
after the compression phase, outputting the liquid at an outlet port at the system pressure during a delivery phase by decreasing the volume of the first cylinder; and
correcting a movement of a piston in the first cylinder of the at least two piston-cylinder units during a compensation phase of the delivery phase based on the measured pressure values.

15. The method of claim 14 further comprising:
determining a correction dependence to correct the movement of the piston in the first cylinder of the at least two piston-cylinder units, the correction dependence being based on a compression coefficient, a pressure and a time value when the compressing or decompressing of the first cylinder is stopped, and another time value at a start of the compensation phase.

16. The method of claim 15, in which the compression coefficient includes a ratio of a change in a pressure to an associated travel distance of the piston in the first cylinder of the at least two piston-cylinder units.

17. The method of claim 16, in which the compression coefficient is calculated using a compression coefficient equation, the compression coefficient equation comprising:

$$Q_c = \Delta s/\Delta P,$$

where $Q_c$ is the compression coefficient, and ΔP is the change in the pressure for the associated travel distance Δs of the piston in the first cylinder of the at least two piston-cylinder units.

18. The method of claim 17, in which the correction dependence is calculated using a correction dependence equation for piston movement, the correction dependence equation for piston movement comprising:

$$s_{corr}(t) = -Q_C \cdot (P_M - P_e) \cdot \left(e^{-\frac{t-t_3}{\tau}} - e^{-\frac{t_5-t_3}{\tau}}\right),$$

where $s_{corr}(t)$ is the correction dependence, t is a time value, $Q_c$ is the compression coefficient, $P_M$ is a pressure at a time $t_3$ in which the measurement phase starts, $t_5$ is a time in which the compensation phase starts, and $P_e$ and τ are both parameters.

19. The method of claim 18, in which the compressing of the liquid in the first cylinder is stopped at the time $t_3$ for the predetermined time interval.

20. The method of claim 18 further comprising:
calculating the parameters $P_e$ and τ using the measured pressure values as a function of time and a method of least squares.

21. The method of claim 18 further comprising:
calculating an effective time constant for the parameter τ using an effective time constant equation, the effective time constant equation comprising:

$$\text{effective time constant} = \tau \cdot \left(1 - k \cdot \frac{Fl}{Fl_{max}}\right)$$

where Fl is a current flow rate, $Fl_{max}$ is a maximum flow rate, and k is a constant factor between 0 and 1; and
inputting the calculated effective time constant into the correction dependence for the parameter τ.

22. The method of claim 14, in which a control device controls the movement of the piston in the first cylinder of the at least two piston-cylinder units.

23. The method of claim 16 further comprising:
supplying the compression coefficient of the liquid to a control device, in which the control device controls the movement of the piston in the first cylinder of the at least two piston-cylinder units.

24. The method of claim 16 further comprising: where the measurement phase occurs during the decompression phase, calculating parameters $P_{eD}$ and $\tau_D$ of the correction dependence using a pressure measurement equation and the measured pressure values as a function of time, the pressure measurement equation comprising:

$$P_{tmess}(t) = P_{MD} + (P_{eD} - P_{MD}) \cdot \left(1 - e^{-\frac{t-t_{21}}{\tau_D}}\right)$$

where $P_{tmess}(t)$ is the measured pressure values as a function of time, t is a time value, $P_{MD}$ is a pressure at a time $t_{21}$ in which the measurement phase starts.

25. The method of claim 24 further comprising:
calculating the correction dependence using a correction dependence equation for piston movement, the correction dependence equation for piston movement including:

$$s_{corr}(t) = -Q_c \cdot (P_M - P_e) \cdot \left(e^{-\frac{t-t_3}{\tau}} - e^{-\frac{t_5-t_3}{\tau}}\right),$$

where $s_{corr}(t)$ is the correction dependence, t is a time value, $Q_c$ is the compression coefficient, $P_M$ is a pressure at a time $t_3$ in which the measurement phase starts, $t_5$ is a time in which the compensation phase starts, and $P_e$ and τ are both parameters; and
converting the parameter $P_{eD}$ of the decompression phase to the parameter $P_e$ of the correction dependence based on a first conversion factor, and converting the parameter $\tau_D$ of the decompression phase to the parameter τ of the correction dependence based on a second conversion factor.

26. The method of claim 25 further comprising:
calculating an effective time constant for the parameter τ using an effective time constant equation, the effective time constant equation comprising:

$$\text{effective time constant} = \tau \cdot \left(1 - k \cdot \frac{Fl}{Fl_{max}}\right)$$

where Fl is a current flow rate, $Fl_{max}$ is a maximum flow rate, and k is a constant factor between 0 and 1; and
inputting the calculated effective time constant into the correction dependence for the parameter τ.

27. A method of pumping a liquid with a piston-pump unit for liquid chromatography, the method comprising:
decompressing a first cylinder of at least two piston-cylinder units during a decompression phase, in which a volume of the first cylinder increases;
compressing the liquid in the first cylinder of the at least two piston-cylinder units during a compression phase, in which a pressure of the liquid changes from a starting pressure to a system pressure;
during a measurement phase of either the compression phase or the decompression phase, measuring piston positions or piston speeds in the first cylinder as a function of time;
during the measurement phase, stopping the compressing or the decompressing of the first cylinder, maintaining a constant pressure value in the volume of the first cylinder for a predetermined time period;
after the compression phase, outputting the liquid at an outlet port at the system pressure during a delivery phase by decreasing the volume of the first cylinder; and
correcting a movement of the piston in the first cylinder of the at least two piston-cylinder units during a compensation phase of the delivery phase based on the measured piston positions or piston speeds in the first cylinder as a function of time.

28. The method of claim 27 further comprising, calculating parameters $s_e$ and τ of the correction dependence using a piston position equation and the measured piston positions in the first cylinder as a function of time, the piston position equation comprising:

$$s_{mess}(t) = (s_M - s_e) \cdot e^{-\frac{t-t_3}{\tau}}$$

where $S_{mess}(t)$ is the measured piston positions in the first cylinder as a function of time, t is a time value, $s_M$ is a piston position at a time $t_3$ in which the measurement phase starts.

29. The method of claim 28 further comprising:
calculating an effective time constant for the parameter τ using an effective time constant equation, the effective time constant equation comprising:

$$\text{effective time constant} = \tau \cdot \left(1 - k \cdot \frac{Fl}{Fl_{max}}\right)$$

where Fl is a current flow rate, $Fl_{max}$ is a maximum flow rate, and k is a constant factor between 0 and 1; and
inputting the calculated effective time constant into the correction dependence for the parameter τ.

* * * * *

UNITED STATES PATENT AND TRADEMARK OFFICE
CERTIFICATE OF CORRECTION

PATENT NO. : 9,624,923 B2
APPLICATION NO. : 13/917963
DATED : April 18, 2017
INVENTOR(S) : Ruegenberg et al.

Page 1 of 1

It is certified that error appears in the above-identified patent and that said Letters Patent is hereby corrected as shown below:

In the Claims

Column 21, In Claim 3, Line 48, delete "claim 1." and insert -- claim 1 --, therefor.

Column 22, In Claim 8, Line 33, delete "$P_{tmess,}(t)$" and insert -- "$P_{tmess}(t)$" --, therefor.

Column 22, In Claim 9, Line 47, delete "Qc," and insert -- $Q_c$ --, therefor.

Column 25, In Claim 21, Line 5, delete "$F1_{max}$," and insert -- $Fl_{max}$, --, therefor.

Signed and Sealed this
Thirty-first Day of March, 2020

Andrei Iancu
*Director of the United States Patent and Trademark Office*